United States Patent [19]

Fujita

[11] 4,355,975

[45] Oct. 26, 1982

[54] ORTHODONTIC APPLIANCE

[76] Inventor: Kinya Fujita, No. 326, Nagasawa, Yokosuka-shi, Kanagawa-ken, Japan

[21] Appl. No.: 216,736

[22] Filed: Dec. 15, 1980

[30] Foreign Application Priority Data

Feb. 8, 1980 [JP] Japan .................................. 55-14414

[51] Int. Cl.³ .............................................. A61C 7/00
[52] U.S. Cl. ........................................ 433/11; 433/13; 433/17
[58] Field of Search .......................... 433/11, 17, 13, 8

[56] References Cited

U.S. PATENT DOCUMENTS

| | | | |
|---|---|---|---|
| 3,091,857 | 6/1963 | Rubin et al. | 433/11 |
| 3,391,461 | 7/1968 | Johnson | 433/17 |
| 3,497,954 | 3/1970 | Kesling | 433/13 |
| 3,838,514 | 10/1974 | Polak | 433/17 |

FOREIGN PATENT DOCUMENTS 1428674  3/1976  United Kingdom .................. 433/13

*Primary Examiner*—Robert Peshock
*Attorney, Agent, or Firm*—Blanchard, Flynn, Thiel, Boutell & Tanis

[57] ABSTRACT

The present invention relates to an orthodontic appliance for the treatment of dental malocclusion. Brackets of the present invention, used for securing the orthodontic wire, are all bonded to the internal sides of the teeth, that is, the lingual or palatal side. The orthodontic appliance comprises a plate bonded to a tooth, which plate is connected to the main body of the bracket. The covering orthodontic cap for fixing the wire is connected to the main body of the bracket. The cap can be removed from the bracket since it is fixed and connected thereto with a connecting part and elastic connecting device. The bracket or the cap is provided with a shearing groove that prevents the caps from sliding off and provides for locking and removal of the cap by simple operations.

9 Claims, 24 Drawing Figures

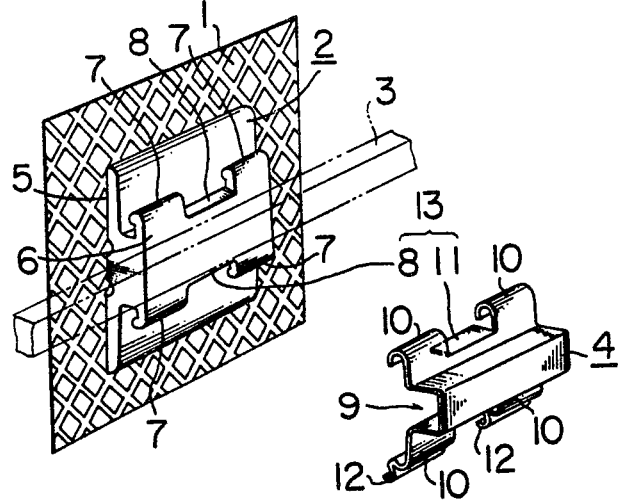
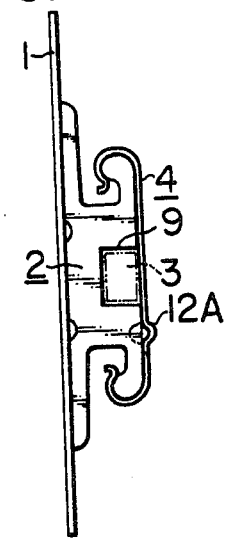
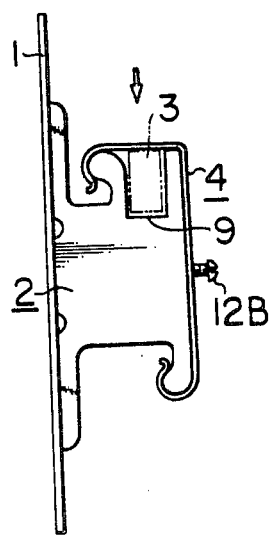
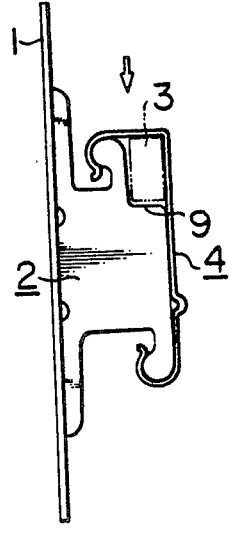
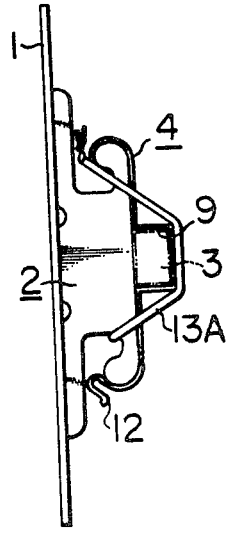

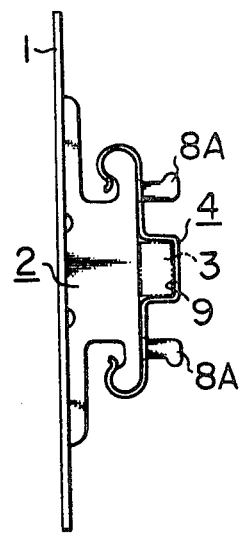
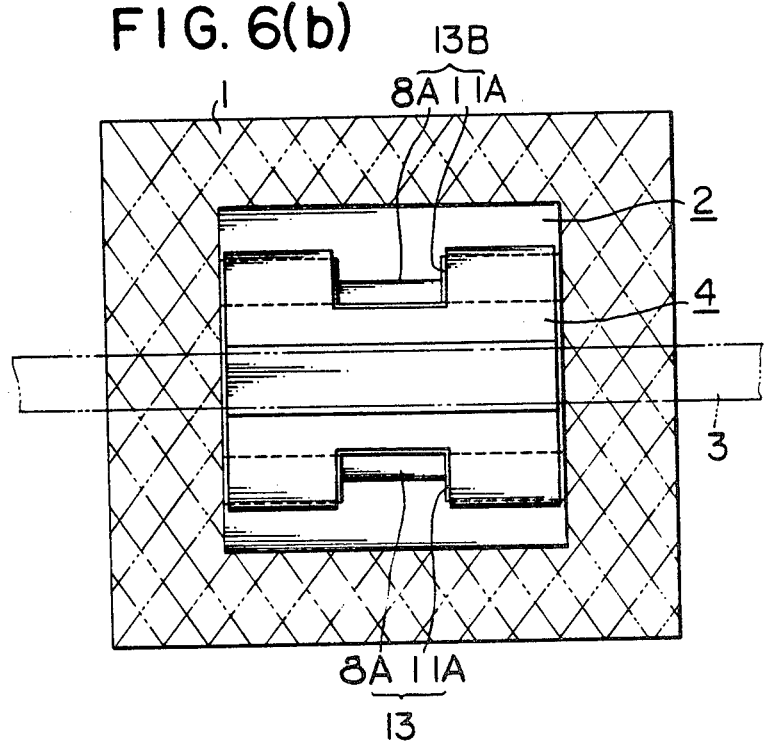

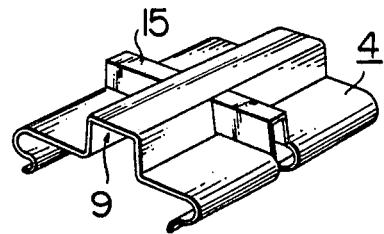
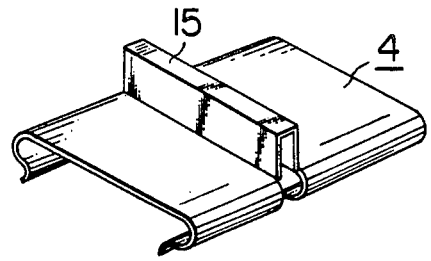
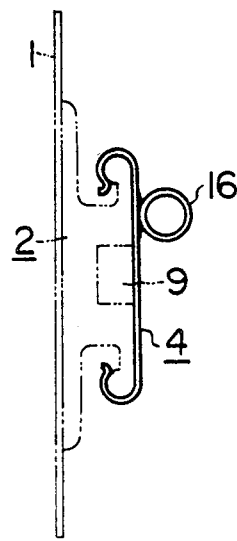
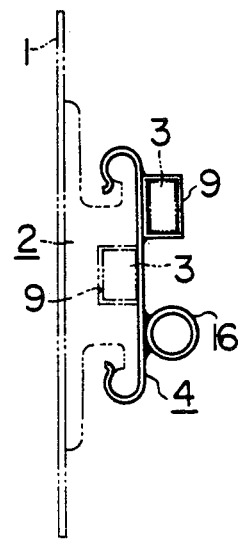
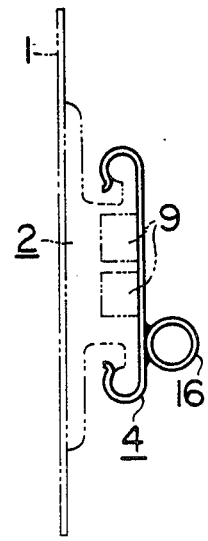

ORTHODONTIC APPLIANCE

The present invention relates to an orthodontic appliance for use in the treatment of dental malocclusion.

The newest and the most effective method of orthodontic treatment, the main purpose of which is to treat dental malocclusion, is the technique of firmly fixing a bracket to each tooth and inserting and fixing a wire into these brackets to correct malalignment of the teeth by the elastic force of the wire. The ribbon arch technique, edgewise technique, Begg technique and the universal technique are known similar procedures, but the main disadvantage of these conventional methods is that the bracket and wire are visible clearly from the outside of the mouth when the mouth is opened, because the brackets are bonded or welded to the outer surfaces of the teeth, that is, their labial or buccal sides. This detracts from the facial beauty of the patient, and accordingly, imposes a considerable psychological burden on the patient. In order to overcome this disadvantage, installation of the brackets on the insides of the teeth is a possibility, but the conventional appliance for installation on the outsides of the teeth is not suitale for installation on the insides of the teeth. It is not only extremely difficult to bond the brackets to the inside surfaces of the teeth, but also insertion of a wire into the grooves of brackets of 3 mm in size from the gingival side, fixation by the ligature wire, and insertion, fixation and cutting of lock pins into brackets are extremely difficult or impossible.

The primary purpose of the present invention is to facilitate orthodontic treatment which is carried out from the lingual or palatal said, to allow insertion, fixation and exchange of wire to be satisfactorily carried out, and to ensure that the wire is firmly fixed. A cap is installed on the bracket so that the cap can be removed easily. In order to achieve the purpose of the invention, the orthodontic wire is fixed by the bracket and the cap. Installation and removal of the wire are easier than in the conventional procedure, so that the manual dental procedure is even easier than the procedure from the lingual side. The psychological burden on patients receiving the orthodontic treatment can be reduced since the cap covers such mechanical parts.

The other purpose of orthodontic the invention is to reduce the number of parts so that the price may be also reduced.

Other purposes and advantages of the present invention will be clarified by the following explanation of the attached Figures.

BRIEF DESCRIPTION OF THE DRAWING

FIG. 1 is a perspective view of an example the orthodontic appliance of the present invention as shown in the first embodiment of the invention.

FIGS. 2, 3, 4 and 5 are side views described in the second, third, fourth and fifth embodiments, respectively.

FIG. 6(a) and FIG. 6(b) show the side and front views, respectively, of the sixth embodiment.

FIGS. 15 and 16 are perspective views of the cap as described in the 15th and 16th embodiments, respectively.

FIGS. 17, 18, 19, 20, 21, and 22 are side views of the 17th, 18th, 19th, 20th, 21st, and 22nd embodiments.

Figure 7:
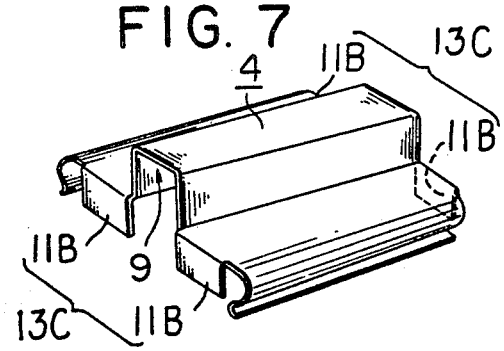
FIG. 7 is a perspective view of the cap as described in the seventh embodiment.

Embodiments of the present invention will be explained with reference to the figures.

FIG. 1 shows a fixing plate (1) having a size of 4–5 mm square and which is attachable to the inside surface of a tooth, namely, the lingual or palatal side, with the aid of a bonding agent. Therefore, the shape of the plate should be slightly curved along the curved line of the dental surface. A bracket (2), having a size of 3–4 mm square, is attached to a side of the fixing plate (1). An orthodontic arch wire (3) is fixed to the bracket (2) by means of a cap (4). The brackets (2) and caps (4) are classified into several fundamental types as described later. The specific embodiments will now be described with reference to the figures.

In the first embodiment, the bracket (2) is somewhat H-shaped in the side view, and the bottom (5) of the bracket is fixed to the fixing plate (1). The upper part of the bracket (6) contacts the wire (3), and the tips at both ends of the upper part (6) serve as hooks (7). The center notch (8) between the hooks (7) is provided for the purpose of preventing sliding of the cap (4). The cap (4) is made of elastic metallic material. On the upper part of the cap (4), a wire holding slot or groove (9) is formed in order to hold the wire 3. The upper and lower ends of the cap (4) are bent to form pairs of C-shaped elastic connection parts (10) which are releasably engageable with the hooks (7). The central portions between the pairs of elastic connection parts (10) have flanges bent inwardly to form tongues (11), and on at least one side of the upper and lower sides of the cap (4), the elastic connection parts (10) are bent in an S-shape to form an unlocking device (12). Sliding prevention unit (13) is composed of the center notch (8) and central tongue (11) of the cap (4) for prevention of horizontal sliding of the cap (4).

The thus-constructed bracket (2) is bonded to the lingual or palatal side of the teeth. Then, the U-shaped orthodontic arch wire (3) is pressed in the caps (4) by pressing it against the upper part (6) of the bracket (2), and then the cap (4) is connected and fixed to the bracket (2) by affixing the elastic connecting parts (10) to the hooks (7). Sliding of the cap (4) is prevented when the central tongue (11) locks the center notch (8). When the wire (3) is removed or exchanged, unlocking device (12) is engaged with the aid of a pin, braced against the bracket (2) and the bottom (5) of the bracket to obtain leverage, and the cap (4) is then removed from the bracket (2).

Other embodiments of the wire holding groove (9), bracket (2), cap (4), means for fixing the cap (4), unlocking device (12) and sliding prevention device (13) will be described.

The wire holding groove (9) in the first embodiment shown in FIG. 1 is part of the cap (4). In contrast FIG. 2 shows a wire fixing groove 9 in the planar part of the upper part (6) of the bracket (2). FIG. 3 shows a wire fixing groove (9) provided in the upper side of the bracket (2), and FIG. 4 shows that a wire fixing groove (9) provided made at the corner of the upper side part of the bracket (2). FIG. 3 and FIG. 4 show the wire fixing groove made so that the wire (3) can be inserted from the occlusal plane (indicated by the arrow) easily and conveniently.

Figure 10:
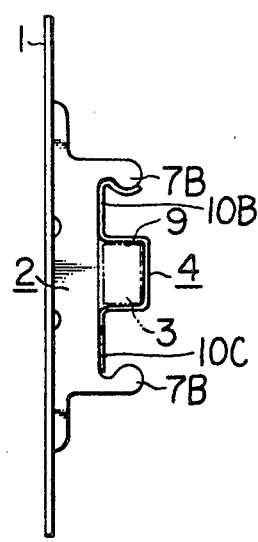
Figure 11:
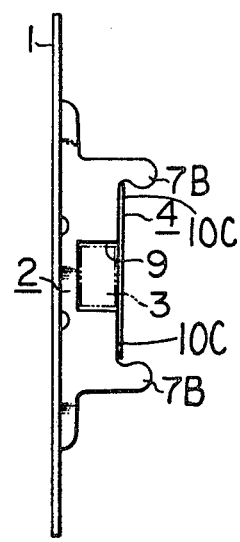
Figure 13:
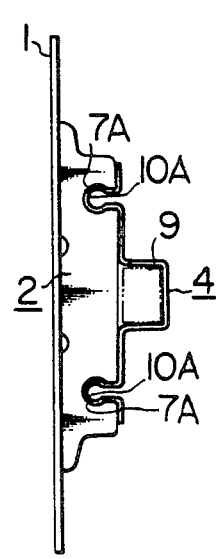
Figure 14:
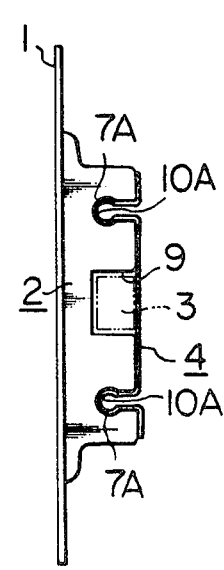

In FIG. 1, bracket (2) and cap (4) are connected by the hooks (7), and cuff piece of elastic connection parts (10). In contrast, FIG. 13 and FIG. 14 show arrangements with grooved brackets (2) having undercut recesses (7A), and wherein the elastic connection parts (10A) are installed in the recesses (7A). FIG. 10 and FIG. 11 show cap-retaining tips (7B) directed inwardly so as to hook the bent elastic connection parts (10B) and straight elastic connection parts (10C), respectively.

Figure 9:
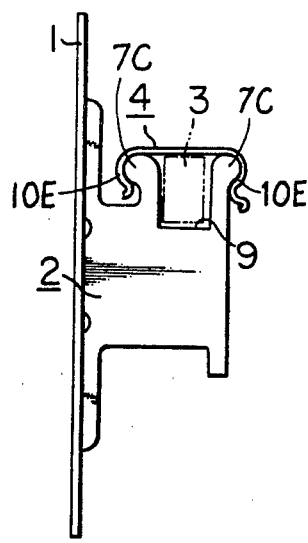
FIGS. 9, 10, 11, 12, 13, and 14 are side views of the 9th, 10th, 11th, 12th, 13th, and 14th embodiments, respectively.
Figure 12:
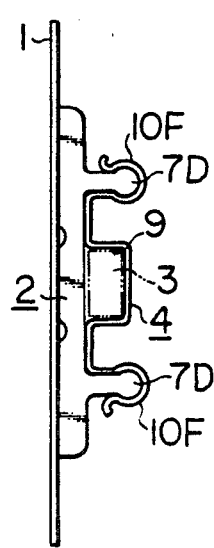

FIG. 9 shows cap-retaining tips (7C) positioned horizontally engaging channel-shaped elastic connection parts (10E). FIG. 12 shows cap-retaining tips with bulbous ends (7D) engaged with mating rounded elastic connection parts (10F).

FIG. 1 shows the first example of the sliding prevention device (13), consisting of the groove at the center (8), and central tongue (11) of the cap (4). FIG. 5 shows an embodiment wherein ligature wire (13A) comprises the sliding prevention device. FIG. 6 (a) and (b) show central protrusions (8A) on the bracket (2) and a central groove (11A) on the cap (4) that comprise the sliding prevention device (13B). FIG. 7 shows side tongues (11B) at the ends of the cap (4) as the sliding prevention device (13C).

The unlocking device (12), in FIG. 1, comprises the S-shaped extension of the cap (4). FIG. 2 shows an unlocking device in which a groove (12A) is provided on the cap (4), opened allowing the cap to be pried off by inserting a pin. FIG. 3 shows a screw (12B) screwed in to lift up the cap (4) to remove it from the bracket.

Figure 8:
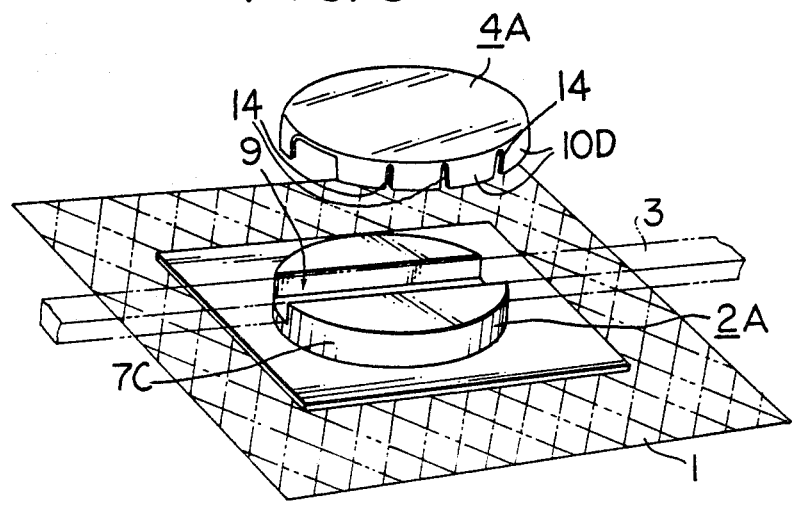
FIG. 8 is a perspective view detailing the parts of the eighth embodiment.

The shape of bracket (2) is rectangular in the above examples, but it may be rounded or elliptical as shown by (2A) in FIG. 8. The cap (4A) should be round or elliptical corresponding to the bracket, and elastic connection part (10D) has narrow grooves (14). The cap (4A) is installed by pushing it over the surface (7C) from both sides, and when the cap is to be removed, the center of the cap (4A) is simply pushed down. The wire groove (9) may be provided on the bracket (2A) or on the cap (4A).

FIG. 15 and FIG. 16 show a U-shaped protrusion (15) for handling and strengthening the cap (4). Such a feature is particularly convenient for a cap (4) having no wire groove (9) as shown in FIG. 16.

Figure 20:
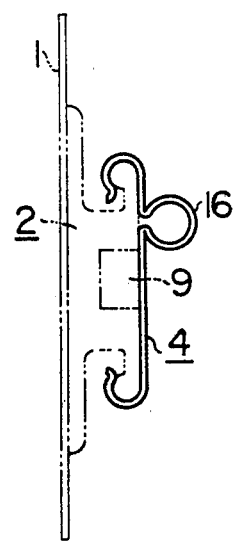
Figure 21:
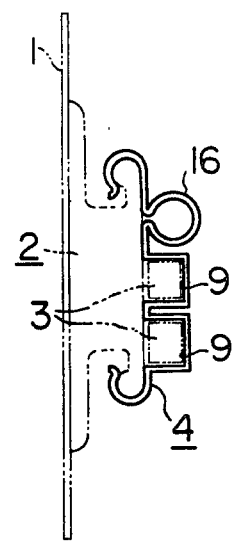
Figure 22:
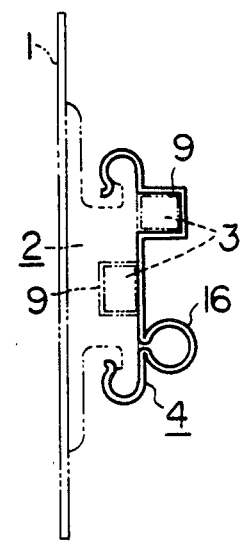

FIG. 17, FIG. 18, FIG. 19, FIG. 20, FIG. 21 and FIG. 22 show a tube (16) on the cap (4) for holding the extra oral anchorage appliance. The tube (16) is cylindrical, a curved wire, round in cross section, is inserted therein to push the teeth. As shown in FIG. 17, FIG. 18 and FIG. 19, the tube (16) may be fixed separately on the cap (4), or as shown in FIG. 20, FIG. 21 and FIG. 22 the tube (16) may be formed from a curved section of the cap (4).

FIG. 18, FIG. 19, FIG. 21 and FIG. 22 show installation of two orthodontic wire grooves (9) with 2 wires (3). As shown in FIG. 18, the wire grooves (9) may be separately formed with other material, or as shown in FIG. 21 and FIG. 22, grooves (9) may be formed and bent from the cap (4). Orthodontic procedures with 2 wires (3) may be accomplished with the appliance excluding the cyrindrical tube (16) shown in FIG. 19, FIG. 21 and FIG. 22 except for the last square set of teeth.

Figure 23:
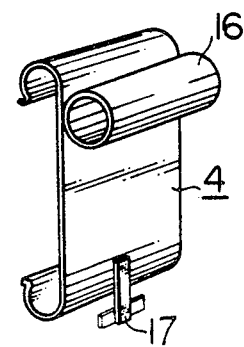
FIG. 23 is a perspective view of the 23rd embodiment.

FIG. 23 shows a protrusion (17) fixed to the cap (4) for securing orthodontic elastics or the like. The protrusion may be tapered, L-shaped, or reversed T-shaped.

The protrusion (17) may be made as a part of the cap (4) by forming it therefrom.

What I claim is:

1. In an orthodontic appliance comprising an upright plate adapted to be fixed to a tooth, a bracket having a surface fixed to said plate and a bracket body extending laterally away from said plate, and an orthodontic arch wire attachable to said bracket body and effective for correcting improper positioning of the tooth, the improvement which comprises the combination: said bracket body has cap-retaining means which are accessible from a direction substantially perpendicular to the lengthwise extent of said orthodontic arch wire, said cap-retaining means being defined by a pair of lips respectively projecting upwardly and downwardly from said bracket body, said lips being undercut on the sides thereof that face said plate so that each lip has an enlarged protuberance at the outer end thereof; an elastically flexible cap removably attached to said bracket body, said cap having elastically flexible connection means releasably interlocked with said cap-retaining means, said elastically flexible connection means being defined by elastic wall portions at the upper and lower ends of said cap with the edges of said elastic wall portions being bent toward each other so that they releasably snugly embrace said enlarged protuberances of said lips, said cap being attachable to and removable from said bracket body by elastic bending of said elastically flexible connection means when said cap is moved in directions respectively toward and away from said cap-retaining means, said bracket body and said cap having cooperating means effective for preventing movement of said cap along said bracket body in a direction lengthwise of said orthodontic arch wire, said cap having removing means for detaching said cap from said bracket body by elastically bending said elastically flexible connection means; said bracket body and said cap having cooperating complementary elongated wall means defining a horizontally elongated groove which is closed at its lateral sides and is open at its longitudinal ends, said orthodontic arch wire extending lengthwise through said groove and being snugly confined therein by said wall means so that said orthodontic arch wire contacts said bracket body, the horizontal length of said groove being several times larger than the width and height of said groove so that the length of the zone of contact between said orthodontic arch wire and said bracket body is several times as large as the width of said orthodontic arch wire.

2. An orthodontic appliance as claimed in claim 1 wherein said groove is rectangular and three sides of said groove are defined by three wall portions of said cap.

3. An orthodontic appliance as claimed in claim 1 wherein said groove is rectangular and three sides of said groove are defined by three wall portions of said bracket.

4. An orthodontic appliance as claimed in claim 1 wherein said groove is rectangular and two sides of the groove are defined by two wall portions of said cap, and the remaining two sides of said groove are defined by two wall portions of said bracket, said groove being located at a corner of said bracket body remote from said plate.

5. In an orthodontic appliance comprising an upright plate adapted to be fixed to a tooth, a bracket having a surface fixed to said plate and a bracket body extending laterally away from said plate, and an orthodontic arch wire attachable to said bracket body and effective for correcting improper positioning of the tooth, the improvement which comprises the combination: said bracket body has cap-retaining means which are accessible from a direction substantially perpendicular to the lengthwise extent of said orthodontic arch wire, said cap-retaining means being defined by a pair of lips both projecting upwardly from said bracket body at horizontally spaced-apart locations, said lips being undercut on the mutually remote sides thereof so that each lip has an enlarged protuberance at the outer end thereof; an elastically flexible cap removably attached to said bracket body, said cap having elastically flexible connection means releasably interlocked with said cap-retaining means, said elastically flexible connection means being defined by elastic wall portions at the opposite horizontal ends of said cap with the edges of said elastic wall portions being bent toward each other so that they releasably snugly embrace said enlarged protuberances of said lips, said cap being attachable to and removable from said bracket body by elastic bending of said elastically flexible connection means when said cap is moved in directions respectively toward and away from said cap-retaining means, said bracket body and said cap having cooperating means effective for preventing movement of said cap along said bracket body in a direction lengthwise of said orthodontic arch wire, said cap having removing means for detaching said cap from said bracket body by elastically bending said elastically flexible connection means; said bracket body and said cap having cooperating complementary elongated wall means defining a horizontally elongated groove which is closed at its lateral sides and is open at its longitudinal ends, said groove being located between said lips, said orthodontic arch wire extending lengthwise through said groove and being snugly confined therein by said wall means so that said orthodontic arch wire contacts said bracket body, the horizontal length of said groove being several times larger than the width and height of said groove so that the length of the zone of contact between said orthodontic arch wire and said bracket body is several times as large as the width of said orthodontic arch wire.

6. In an orthodontic appliance comprising an upright plate adapted to be fixed to a tooth, a bracket having a surface fixed to said plate and a bracket body extending laterally away from said plate, and an orthodontic arch wire attachable to said bracket body and effective for correcting improper positioning of the tooth, the improvement which comprises the combination: said bracket body has cap-retaining means which are accessible from a direction substantially perpendicular to the lengthwise extent of said orthodontic arch wire, said cap-retaining means being defined by a pair of lips projecting horizontally from said bracket body in a direction away from said plate at locations close to the upper and lower ends of said bracket body, said lips being undercut on the opposing sides thereof so that each lip has an enlarged protuberance at the outer end thereof; and elastically flexible cap removably attached to said bracket body, said cap having elastically flexible connection means releasably interlocked with said cap-retaining means, said elastically flexible connection means being defined by elastic wall portions receivable in said undercut recesses inwardly of said protuberances, said cap being attachable to and removable from said bracket body by elastic bending of said elastically flexible connection means when said cap is moved in directions respectively toward and away from said cap-retaining means, said bracket body and said cap having cooperating means effective for preventing movement of said cap along said bracket body in a direction lengthwise of said orthodontic arch wire, said cap having removing means for detaching said cap from said bracket body by elastically bending said elastically flexible connection means; said bracket body and said cap having cooperating complementary elongated wall means defining a horizontally elongated groove which is closed at its lateral sides and is open at its longitudinal ends, said orthodontic arch wire extending lengthwise through said groove and being snugly confined therein by said wall means so that said orthodontic arch wire contacts said bracket body, the horizontal length of said groove being several times larger than the width and height of said groove so that the length of the zone of contact between said orthodontic arch wire and said bracket body is several times as large as the width of said orthodontic arch wire.

7. In an orthodontic appliance comprising an upright plate adapted to be fixed to a tooth, a bracket having a surface fixed to said plate and a bracket body extending laterally away from said plate, and an orthodontic arch wire attachable to said bracket body and effective for correcting improper positioning of the tooth, the improvement which comprises the combination: said bracket body has an upper wall and a lower wall extending away from said plate and an upright wall remote from said plate, said upper wall having three wall portions defining three sides of a rectangular groove, the wall portion closest to said plate being undercut on the side thereof facing said plate to define a first lip having an enlarged first protuberance at its upper end, a second lip extending downwardly from said lower wall, said second lip being undercut on the side thereof facing said plate to define an enlarged second protuberance at its lower end, said lips defining cap-retaining means which are accessible from a direction substantially perpendicular to the lengthwise extent of said orthodontic arch wire; an elastically flexible cap removably attached to said bracket body, said cap being substantially L-shaped in cross section and having an upright wall resting against the upright wall of said bracket body and an upper horizontal wall resting on said upper wall of said bracket body, said cap having first and second elastic wall portions at the ends of its upright and horizontal walls, said first and second elastic wall portions snugly releasably embracing said first and second protuberances and extending into the undercuts thereof, respectively, said first and second elastic wall portions defining elastically flexible connection means releasably interlocked with said cap-retaining means, said cap being attachable to and removable from said bracket body by elastic bending of said elastically flexible connection means when said cap is moved in directions respectively toward and away from said cap-retaining means, said bracket body and said cap having cooperating means effective for preventing movement of said cap along said bracket body in a direction lengthwise of said orthodontic arch wire, said cap having removing means for detaching said cap from said bracket body by elastically bending said elastically flexible connection means; said three wall portions of said bracket body and a portion of said upper horizontal wall of said cap defining cooperating complementary elongated wall means defining said groove which is horizontally elongated, closed at its lateral sides and open at its longitudinal ends, said orthodontic arch wire extending lengthwise through said groove and being snugly confined therein by said wall means so that said orthodontic arch wire contacts said bracket body, the horizontal length of said groove being several times larger than the width and height of said groove so that the length of the zone of contact between said orthodontic arch wire and said bracket body is several times as large as the width of said orthodontic arch wire.

8. An orthodontic appliance according to claim 1, claim 5, claim 6 or claim 7, wherein said cap has a substantially U-shaped, upright protrusion projecting in a direction away from said plate.

9. An orthodontic appliance according to claim 1, claim 5, claim 6 or claim 7 in which said cooperating means for preventing movement of said cap along said bracket body comprises a notch formed by a cut-away portion of one of said lips and a tongue formed by a bent wall portion of said cap and extending into said notch.

* * * * *